(12) United States Patent
Jeong et al.

(10) Patent No.: US 9,638,609 B2
(45) Date of Patent: May 2, 2017

(54) APPARATUS FOR PROVIDING SAMPLE GAS AND RELATED METHODS

(71) Applicant: Samsung Electronics Co., Ltd., Gyeonggi-do (KR)

(72) Inventors: Jong-Cheol Jeong, Namyangju-si (KR); Kyung-Hwan Jeong, Hwaseong-si (KR); Jong-Soo Kim, Suwon-si (KR); Pil-Kwon Jun, Seoul (KR)

(73) Assignee: Samsung Electronics Co., Ltd. (KR)

( * ) Notice: Subject to any disclaimer, the term of this patent is extended or adjusted under 35 U.S.C. 154(b) by 478 days.

(21) Appl. No.: 14/148,331

(22) Filed: Jan. 6, 2014

(65) Prior Publication Data

US 2014/0206097 A1 Jul. 24, 2014

(30) Foreign Application Priority Data

Jan. 18, 2013 (KR) ........................ 10-2013-0006003

(51) Int. Cl.
*G01N 1/22* (2006.01)
*G01N 33/00* (2006.01)

(52) U.S. Cl.
CPC ........... *G01N 1/22* (2013.01); *G01N 33/0009* (2013.01); *G01N 33/0011* (2013.01); *Y10T 137/87619* (2015.04); *Y10T 436/25875* (2015.01)

(58) Field of Classification Search
CPC ...................................................... G01N 1/22
USPC ........................................................ 436/181
See application file for complete search history.

(56) References Cited

U.S. PATENT DOCUMENTS

| | | | | |
|---|---|---|---|---|
| 3,995,162 | A * | 11/1976 | Peterson | G21K 5/10 250/385.1 |
| 5,353,323 | A * | 10/1994 | Hirokawa | G21K 5/02 378/34 |
| 6,881,952 | B2 | 4/2005 | Kim | |
| 7,566,422 | B2 * | 7/2009 | Hara | G05D 16/2013 118/50.1 |
| 8,191,402 | B2 | 6/2012 | Kishita et al. | |
| 2012/0255855 | A1 * | 10/2012 | Bjornard | C23C 14/0073 204/192.1 |

FOREIGN PATENT DOCUMENTS

| | | |
|---|---|---|
| JP | 2009-210436 | 9/2009 |
| JP | 2011-007534 | 1/2011 |
| JP | 2011-043461 | 3/2011 |

(Continued)

*Primary Examiner* — Christopher A Hixson
*Assistant Examiner* — Emily Berkeley
(74) *Attorney, Agent, or Firm* — Myers Bigel, P.A.

(57) ABSTRACT

An apparatus for providing a sample gas includes a gas dosing part, a first pressure gauge for measuring a pressure of a sample gas dosed through the gas dosing part, a plurality of flow lines positioned between the gas dosing part and a gas analyzer that can be opened or closed according to the pressure measured by the first pressure gauge, a plurality of control valves respectively formed in the plurality of flow lines and controlling the plurality of flow lines to be opened or closed, a bypass line formed on at least one of the plurality of flow lines and exhausting some of the sample gas flowing along the flow lines, and a controller for selecting one of the plurality of flow lines according to the pressure measured by the first pressure gauge and controlling the control valves formed in the selected flow line.

3 Claims, 11 Drawing Sheets

(56) References Cited

FOREIGN PATENT DOCUMENTS

| KR | 101998072272 | 11/1998 |
|----|--------------|---------|
| KR | 1020060042741 | 5/2006 |
| KR | 100511948 | 8/2008 |
| KR | 1020110017654 | 2/2011 |

* cited by examiner

Ion Source

Mass Filter

Detector

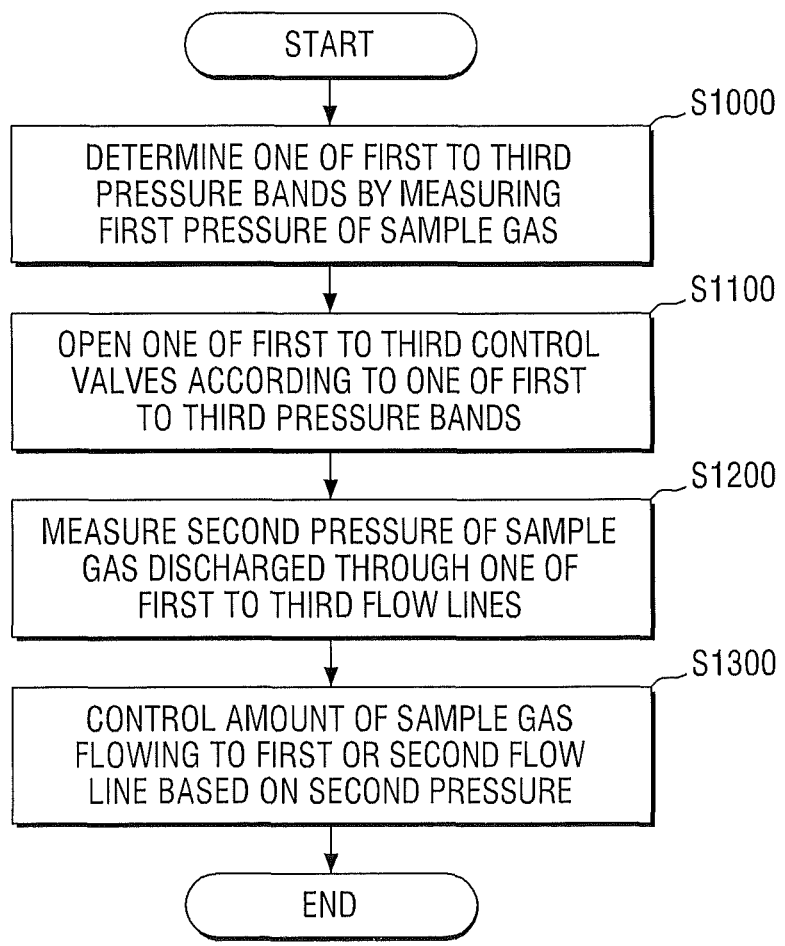

APPARATUS FOR PROVIDING SAMPLE GAS AND RELATED METHODS

CROSS-REFERENCE TO RELATED APPLICATION

This application claims priority under 35 U.S.C. 119 from Korean Patent Application No. 10-2013-0006003, filed on Jan. 18, 2013, the content of which is incorporated by reference herein in its entirety.

FIELD

The present inventive concept relates to apparatus for providing a sample gas and related methods.

BACKGROUND

In semiconductor manufacturing equipment, chemical reactions of various kinds of gases are used to form layers on a wafer board. A process chamber where chemical reactions take place, should be in conditions in which contaminant materials and unnecessary elements are not present.

Recently, semiconductor devices are becoming integrated, and the manufacturing yield of semiconductor devices may be lowered due to a small difference in processing conditions of the process chamber. For example, after layers are deposited or etched by reactions between gases, gases remaining in forms of unreacted gases or reaction byproducts may affect subsequent processes, causing a reduction in the yield or other failures.

Therefore, in order to control in advance various failures which may occur in the semiconductor manufacturing process or to identify a state of an ongoing process, it is desirable to monitor changes in chemical components and concentrations of gases in the process chamber on a real time basis.

A residual gas analyzer (RGA) analyzes the components and concentration of a sample gas by sampling some of the gas flowing in a vent line after a reaction takes place in a process chamber, decomposing the sample gas into a radical gas using high voltage energy and measuring a mass of the decomposed gas. That is to say, the components and concentration of the sample gas are analyzed by measuring a current value of positive ions of ionized sample gas. In addition to the residual gas analyzer (RGA), an on-line time-of-flight (ToF) analyzer, or a Fourier Transform Infrared (FT-IR) analyzer may also be used to analyze the components and concentration of the sample gas.

SUMMARY

The present inventive concept provides apparatus for providing a sample gas, which can provide the sample gas to a gas analyzer, irrespective of the pressure band of the sample gas.

The present inventive concept also provides methods for providing a sample gas, which can provide the sample gas to a gas analyzer, irrespective of the pressure band of the sample gas.

According to an aspect of the present inventive concept, there is provided an apparatus for providing a sample gas to a gas analyzer, the apparatus including a gas dosing part, a first pressure gauge for measuring a pressure of a sample gas dosed through the gas dosing part, a plurality of flow lines positioned between the gas dosing part and a gas analyzer and configured to be opened or closed according to the pressure measured by the first pressure gauge, a plurality of control valves respectively formed in the plurality of flow lines and configured to be opened or closed to open or close a respective flow line, a bypass line formed on at least one of the plurality of flow lines and exhausting some of the sample gas flowing along the flow lines, and a controller configured to select one of the plurality of flow lines according to the pressure measured by the first pressure gauge and to control the control valves formed in the selected flow lines.

According to another aspect of the present inventive concept, there is provided an apparatus for providing a sample gas to a gas analyzer. The apparatus includes a gas dosing portion, a first pressure gauge for measuring a pressure of a sample gas provided through the gas dosing portion, first, second and third control valves configured to be opened and closed, and a controller. The first control valve is disposed in a first flow line that extends between the gas dosing portion and the gas analyzer, the second control valve is disposed in a second flow line that extends between the gas dosing portion and the gas analyzer, and the third control valve is disposed in a third flow line that extends between the gas dosing portion and the gas analyzer. The controller is configured to: open the first control valve when the pressure measured by the first pressure gauge is in a first pressure band, thereby allowing the sample gas to flow through the first flow line; open the second control valve when the pressure measured by the first pressure gauge is in a second pressure band, thereby allowing the sample gas to flow through the second flow line; and open the third control valve when the pressure measured by the first pressure gauge is in a third pressure band, thereby allowing the sample gas to flow through the third flow line.

According to still another aspect of the present inventive concept, there is provided a method for providing a sample gas to a gas analyzer. The method includes: providing an apparatus comprising first, second and third flow lines with each flow line extending between a gas dosing portion and a gas analyzer; measuring a first pressure of dosed sample gas in the gas dosing portion; determining one of first, second and third pressure bands based on the measured first pressure; selecting one of the first, second and third flow lines based on the determined pressure band; opening a control valve in the selected flow line; flowing the sample gas through the selected flow line; measuring a second pressure of the sample gas exhausted through the selected flow line; and controlling an amount of the sample gas flowing to the first or second flow line, if selected, based on the measured second pressure.

BRIEF DESCRIPTION OF THE DRAWINGS

The above and other features and advantages of the present inventive concept will become more apparent by describing in detail preferred embodiments thereof with reference to the attached drawings in which:

FIG. 10 is a flowchart sequentially illustrating a method for providing a sample gas according to an embodiment of the present inventive concept.

DETAILED DESCRIPTION OF THE EMBODIMENTS

Figure 1A:
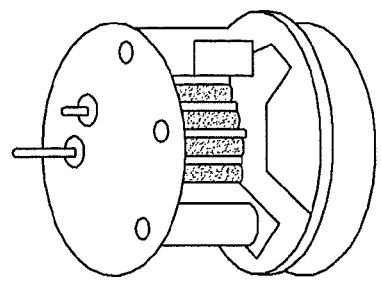
FIG. 1A illustrates an ion source of a residual gas analyzer (RGA)

The present inventive concept will now be described more fully hereinafter with reference to the accompanying drawings, in which preferred embodiments of the inventive concept are shown. This inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art. The same reference numbers indicate the same components throughout the specification. In the attached figures, the thickness of layers and regions may be exaggerated for clarity.

It will be understood that when an element is referred to as being "on" another element, it can be directly on the other element, or intervening elements may also be present. In contrast, when an element is referred to as being "directly on" another element, there are no intervening elements present.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The use of the terms "a" and "an" and "the" and similar referents in the context of describing the inventive concept (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Unless defined otherwise, all technical and scientific terms used herein have the same meaning as commonly understood by one of ordinary skill in the art to which this inventive concept belongs. It is noted that the use of any and all examples, or exemplary terms provided herein is intended merely to better illuminate the inventive concept and is not a limitation on the scope of the inventive concept unless otherwise specified.

The present inventive concept will be described with reference to perspective views, cross-sectional views, and/or plan views, in which preferred embodiments of the inventive concept are shown. Thus, the profile of an exemplary view may be modified according to manufacturing techniques and/or allowances. That is, the embodiments of the invention are not intended to limit the scope of the present inventive concept but cover all changes and modifications that can be caused due to a change in manufacturing process. Thus, regions shown in the drawings are illustrated in schematic form and the shapes of the regions are presented simply by way of illustration and not as a limitation.

Embodiments of the present inventive concept relating to apparatus for providing a sample gas and methods of using the same, which will be described below, are directed to an interface device positioned between a process chamber and a gas analyzer, which can maintain a pressure of a sample gas dosed into the gas analyzer at a constant level to facilitate the operation of the gas analyzer.

In semiconductor manufacturing process steps, the process steps are performed in a variety of pressure bands ranging from a highly vacuum state to an atmospheric pressure. However, in view of intrinsic characteristics of gas analyzers, some gas analyzers may operate only in pressure bands of a highly vacuum state, and other gas analyzers may operate only in the atmospheric pressure band. Therefore, in order to use a gas analyzer for process analysis, a sample gas providing apparatus may need to be newly constructed for each pressure band, and there is a limit in monitoring various process steps on a real time basis due to a difference in the reaction time between the process steps. Embodiments of the present inventive concept provide sample gas providing apparatus which can be used in all pressure bands. There are several types of gas analyzers, including a residual gas analyzer (RGA), an optical emission spectrometry (OES) analyzer, and so on, but the following description will be made with regard to only the RGA. Since the RGA operates in a low pressure band and has a high detection limit, it can be used in evaluating a process step performed in a low pressure band, such as etching, or monitoring leakage occurring in a metal deposition apparatus.

Figure 1B:
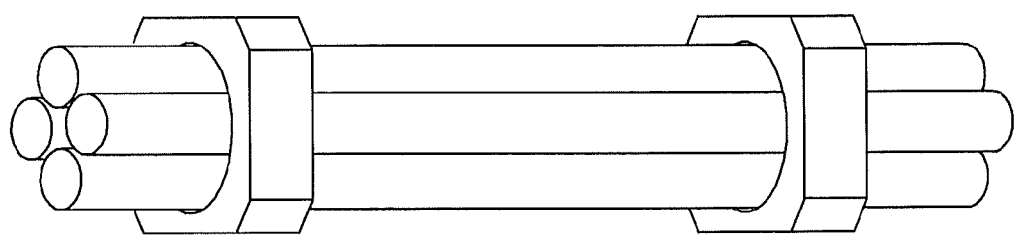
FIG. 1B illustrates a mass filter of a RGA.
Figure 1C:
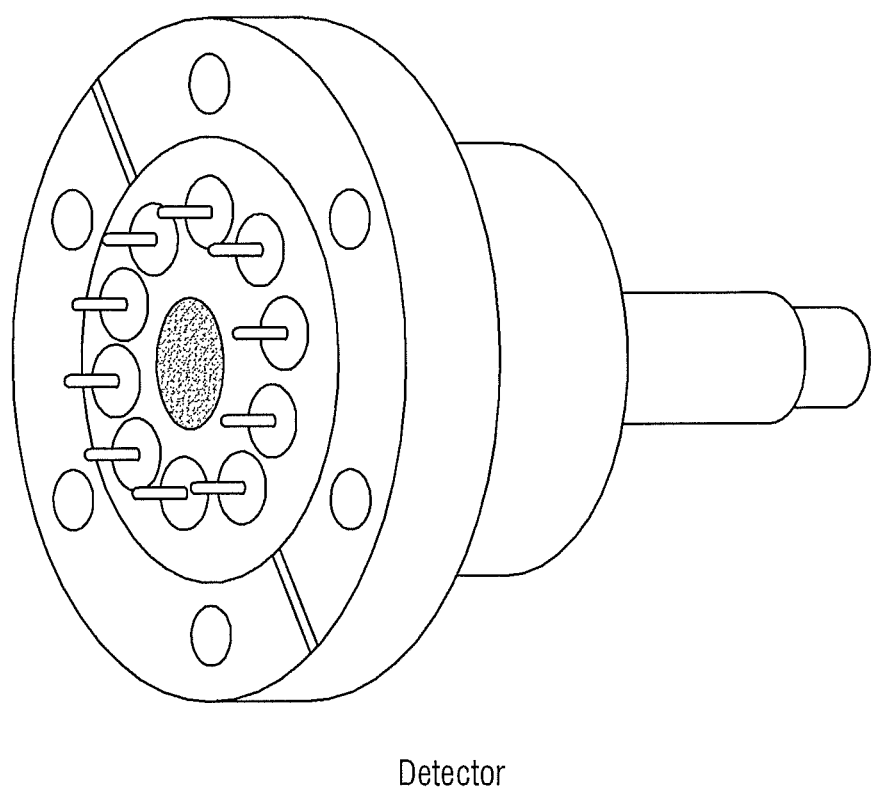
FIG. 1C illustrates a detector of a RGA.

Hereinafter, an apparatus for providing a sample gas according to a first embodiment of the present inventive concept will be described with reference to FIGS. 1A to 1C. FIG. 1A illustrates an ion source of a residual gas analyzer (RGA), FIG. 1B illustrates a mass filter of the RGA, and FIG. 1C illustrates a detector of the RGA.

Referring to FIG. 1A, a sample gas is dosed into an introduction part of the RGA, and the sample gas dosed from ion source collides with electrons, so that the dosed sample gas is ionized. Referring to FIG. 1B, components of the ionized sample gas are distinguished by a mass filter. In particular, the mass of the ionized sample gas is measured, thereby distinguishing the components of the ionized sample gas by mass. Referring to FIG. 1C, a detector reads a value of current generated when the ionized sample gas flows, thereby measuring the concentration of the ionized sample gas.

In a case where a semiconductor manufacturing process is performed in a high vacuum state, since a small amount of sample gas is induced into the RGA introduction part, a serious problem may not be raised. However, in a case where a semiconductor manufacturing process is performed at a high pressure (e.g., 10 torr or higher), an amount of sample gas induced into the RGA introduction part is increased, thereby potentially contaminating the ion source of RGA and lowering the sensitivity of the ion source. In particular, a filament of the ion source may be broken. In this case, the RGA can be used even in the high vacuum state by additionally installing a separate device for adjusting the amount of sample gas induced into the RGA introduction part. In an example embodiment of the separate device, a capillary tube may be installed in the RGA introduction part. When the sample gas is induced into the RGA introduction part through the capillary tube, the amount of sample gas induced into the RGA introduction part can be reduced. However, the flow rate of sample gas is also reduced, so that a response time is also reduced due to a difference between a time at which gas is generated in a process chamber and a time at which the gas induced into the RGA introduction part is measured, thereby making it difficult to measure the amount of sample gas induced into the RGA introduction part on a real time basis. In addition, the capillary tube may clog due to powder contained in the gas exhausted from the process chamber.

Further, if there a considerable change in the pressure bands while a particular process is performed, sample gas measured data may not be obtained from some pressure bands. In another example embodiment of the separate device, a gas dosing valve may be installed in the RGA introduction part. The use of the gas dosing valve may allow the sample gas providing apparatus to be employed even in a case where there is a considerable change in the pressure bands. However, the gas dosing valve should be manually operated, and an error may be created while the gas dosing valve is manually operated. Instead of the conventional RGA gas dosing device, sample gas providing apparatus according to the present inventive concept may be used over the entire range of pressure bands. Hereinafter, an embodiment of the sample gas providing apparatus according to the present inventive concept will be described.

Figure 2:
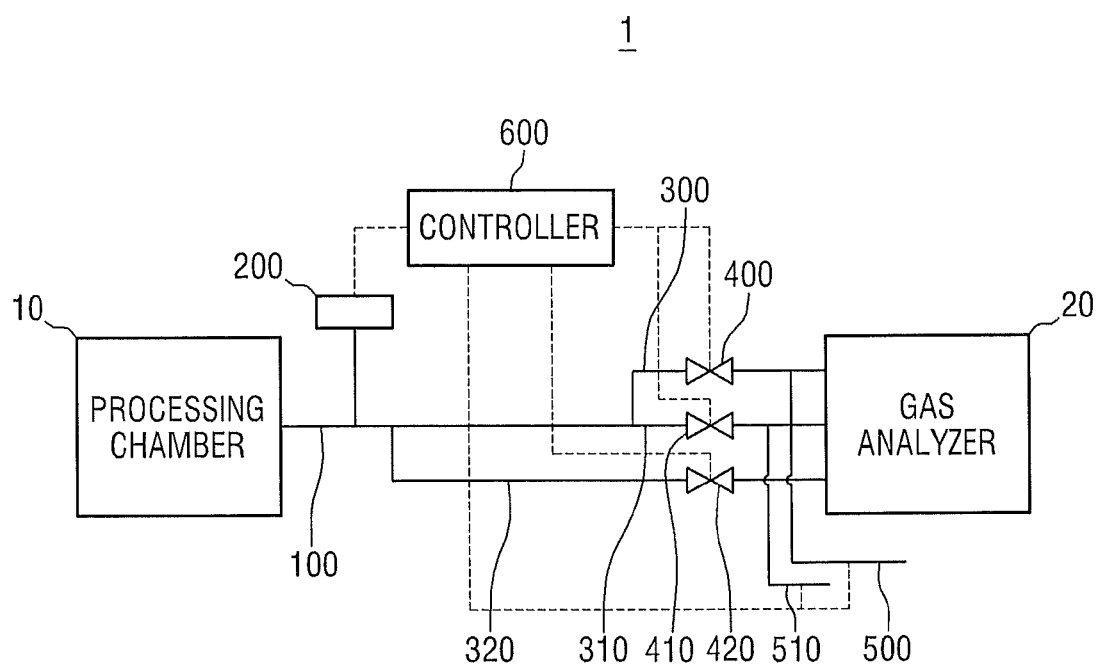
FIG. 2 schematically illustrates a apparatus for providing a sample gas according to an embodiment of the present inventive concept.
Figure 3:
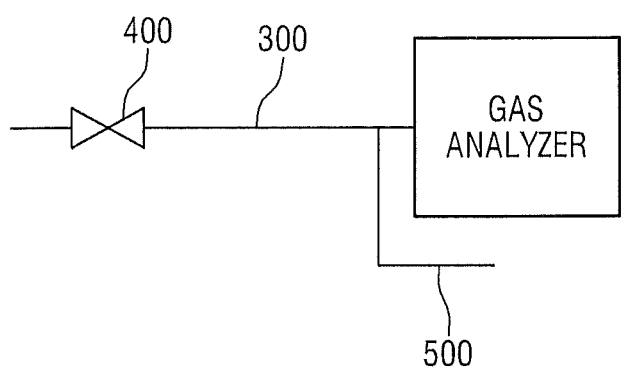
FIG. 3 illustrates a portion of the apparatus for providing a sample gas shown in FIG. 2.
Figure 4:
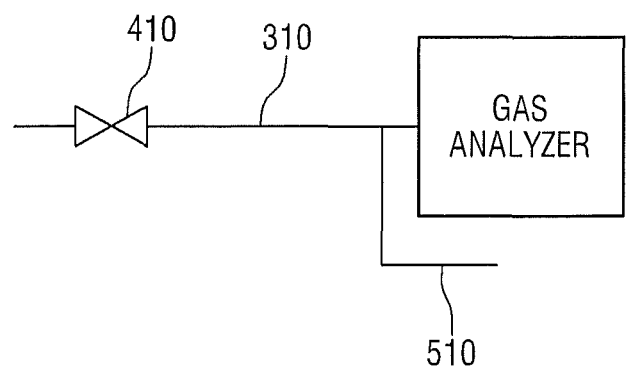
FIG. 4 illustrates a portion of the apparatus for providing a sample gas shown in FIG. 2.
Figure 5:
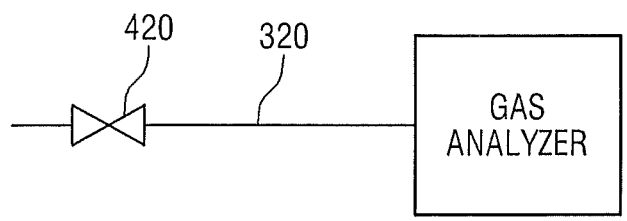
FIG. 5 illustrates a portion of the apparatus for providing a sample gas shown in FIG. 2.
Figure 6:
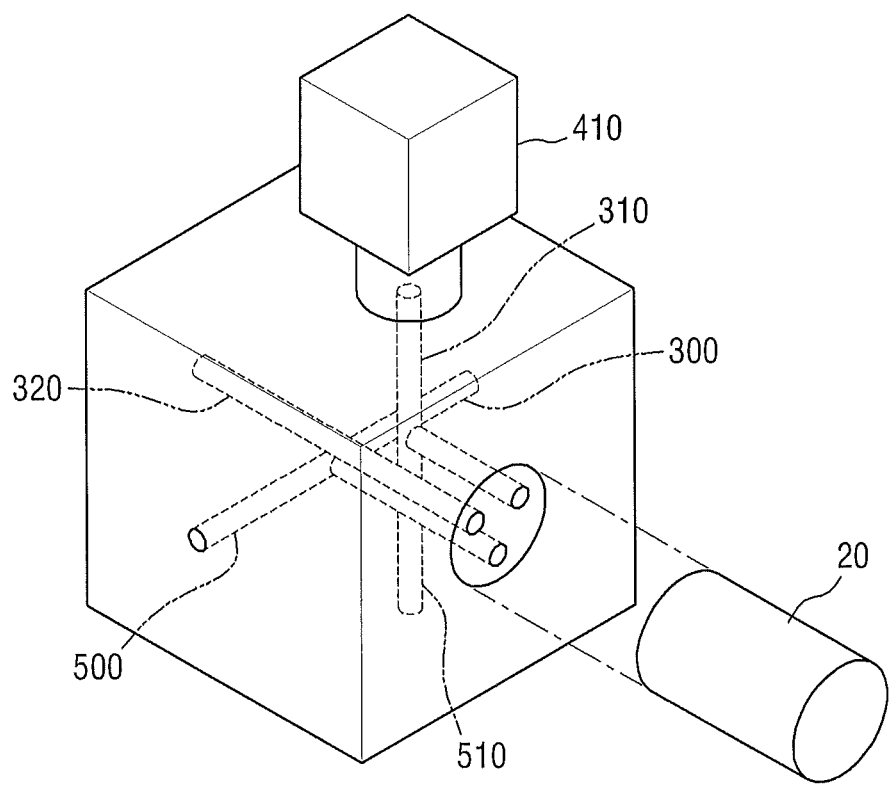
FIG. 6 illustrates a portion of the apparatus for providing a sample gas shown in FIG. 2 in three dimensions.

FIG. 2 schematically illustrates an apparatus for providing a sample gas according to an embodiment of the present inventive concept, FIG. 3 illustrates a portion of the apparatus for providing a sample gas shown in FIG. 2, FIG. 4 illustrates a portion of the apparatus for providing a sample gas shown in FIG. 2, FIG. 5 illustrates a portion of the apparatus for providing a sample gas shown in FIG. 2, and FIG. 6 illustrates a portion of the apparatus for providing a sample gas shown in FIG. 2 in a three dimensional way.

Referring to FIGS. 2 to 6, the sample gas providing apparatus 1 includes a gas dosing part, portion or section 100, a first pressure gauge 200, a first flow line 300, a second flow line 310, a third flow line 320, a first control valve 400, a second control valve 410, a third control valve 420, a first bypass line 500, a second bypass line 510, and a controller 600.

The gas dosing part 100 is a path through which the gas is induced to the sample gas providing apparatus 1. The gas dosing part 100 is connected to the process chamber 10, and the remaining gas or the reaction byproduct after the reaction is completed in the process chamber 10 is induced into the sample gas providing apparatus 1 through the gas dosing part 100.

The first pressure gauge 200 measures the pressure of the sample gas induced through the gas dosing part 100. The first pressure gauge 200 determines one of first to third pressure bands p1, p2 and p3 based on the measured pressure. As will be described below, one of first to third control valves 400, 410 and 420 may be controlled by the controller 600 using one of the first to third pressure bands p1, p2 and p3. That is to say, one of first to third flow lines 300, 310 and 320 is opened by one of the first to third control valves 400, 410 and 420 to allow the sample gas to flow through the opened flow line.

In addition, the first pressure band p1 may be a band greater than or equal to 500 torr, the second pressure band p2 may be a band greater than or equal to 1 torr and less than 500, and the third pressure band p3 may be a band less than 1 torr. In dividing the pressure bands in the above-stated manner, intrinsic pressure bands of various manufacturing processes, including deposition, etching, annealing, and so on, are taken into consideration.

The first flow line 300 is positioned between the gas dosing part 100 and the gas analyzer 20. If the pressure measured by the first pressure gauge 200 is in the first pressure band p1, the sample gas is fed through the first flow line 300. For example, the sample gas may be an unreacted gas in the process chamber 10 or gas remaining in the form of reaction byproducts. When the first control valve 400 opens the first flow line 300, the sample gas is fed to the gas analyzer 20. The gas analyzer 20 is an apparatus for analyzing the components and concentration of the sample gas. In a case where the sample gas is a corrosive reaction gas (e.g., HCL, HBr, etc.) or a special reaction gas having high reactivity or resolvability (e.g., $SiH_4$, $B_2H_6$, organic metal gas, etc.), the first flow line 300 may be made of a stable material having good corrosion resistance and being barely reactive (e.g., substantially non-reactive). For example, the first flow line 300 may be a stainless steel tube (e.g., a SUS 316L-EP tube having a $Cr_2O_3$ passivation layer formed thereon). In addition, the first flow line 300 may be made of a stainless steel material (e.g., ⅛ inch SUS material), and may include a quadrupole arrangement having 4 poles arranged in parallel with each other. The quadrupole arrangement is an apparatus configured to allow only elements each having a particular mass to pass the poles and the other elements to be removed when they collide with the poles by simultaneously applying a DC voltage and an RF voltage having opposite polarities and having a phase difference of 180° to neighboring poles. Therefore, it is possible to prevent the first flow line 300 from clogging by powder by forming the first flow line 300 using a stainless steel tube (e.g., a ⅛ inch SUS tube) having a quadrupole arrangement.

The second flow line 310 is positioned between the gas dosing part 100 and the gas analyzer 20. If the pressure measured by the first pressure gauge 200 is in the second pressure band p2, the sample gas is fed through the second flow line 310. When the second control valve 410 opens the second flow line 310, the sample gas is fed to the gas analyzer 20. In a case where the sample gas is a corrosive reaction gas (e.g., HCL, HBr, etc.) or a special reaction gas having high reactivity or resolvability (e.g., $SiH_4$, $B_2H_6$, organic metal gas, etc.), the second flow line 310 may be made of a stable material having good corrosion resistance and being barely reactive (e.g., substantially non-reactive). For example, the second flow line 310 may be a stainless steel tube (e.g., a SUS 316L-EP tube having a $Cr_2O_3$ passivation layer formed thereon). In addition, the second flow line 310 may be made of a stainless steel material (e.g., ⅛ inch SUS material), and may include a quadrupole arrangement. Therefore, it is possible to prevent the second flow line 310 from clogging by powder by forming the second flow line 310 using a stainless steel tube (e.g., a ⅛ inch SUS tube) having a quadrupole arrangement.

The third flow line 320 is positioned between the gas dosing part 100 and the gas analyzer 20. If the pressure measured by the first pressure gauge 200 is in the third pressure band p3, the sample gas is fed through the third flow line 320. When the third control valve 420 opens the third flow line 320, the sample gas is fed to the gas analyzer 20. In a case where the sample gas is a corrosive reaction gas (e.g., HCL, HBr, etc.) or a special reaction gas having high reactivity or resolvability (e.g., $SiH_4$, $B_2H_6$, organic metal gas, etc.), the third flow line 320 may be made of a stable material having good corrosion resistance and being barely reactive (e.g., substantially non-reactive). For example, the third flow line 320 may be a stainless steel tube (e.g., a SUS 316L-EP tube having a $Cr_2O_3$ passivation layer formed thereon). In addition, the third flow line 320 may be made of a stainless steel material (e.g., ⅛ inch SUS material), and may include a quadrupole arrangement. Therefore, it is possible to prevent the third flow line 320 from clogging by powder by forming the third flow line 320 using a stainless steel tube (e.g., a ⅛ inch SUS tube) having a quadrupole arrangement.

The first control valve 400 is formed in the first flow line 300 and allows or controls the first flow line 300 to be opened or closed. When the sample gas in the first pressure band p1 is induced, the first control valve 400 is opened by the controller 600 to allow the sample gas to flow along the first flow line 300.

The second control valve 410 is formed in the second flow line 310 and allows or controls the second flow line 310 to be opened or closed. When the sample gas in the second pressure band p2 is induced, the second control valve 410 is opened by the controller 600 to allow the sample gas to flow along the second flow line 310. For example, the second control valve 410 may be an automatic valve. The automatic valve is a valve for automatically controlling the opening and closing rate to maintain a preset pressure.

The third control valve 420 is formed in the third flow line 320 and allows or controls the third flow line 320 to be opened or closed. When the sample gas in the third pressure band p3 is induced, the third control valve 420 is opened by the controller 600 to allow the sample gas to flow along the third flow line 320.

The first bypass line 500 is formed in the first flow line 300 and exhausts some of the sample gas flowing along the first flow line 300. When the sample gas in the first pressure band p1 is induced, the sample gas flows along the first flow line 300, and the first bypass line 500 reduces the pressure by reducing an amount of the sample gas reaching the gas analyzer 20 and adjusts the flow rate of the sample gas.

The second bypass line 510 is formed in the second flow line 310 and exhausts some of the sample gas flowing along the second flow line 310. When the sample gas in the second pressure band p2 is induced, the sample gas flows along the second flow line 310, and the second bypass line 510 reduces the pressure by reducing an amount of the sample gas reaching the gas analyzer 20 and adjusts the flow rate of the sample gas.

The controller 600 controls one of the first to third control valves 400, 410 and 420 according to one of the first to third pressure bands p1, p2 and p3 determined by the first pressure gauge 200. For example, if the pressure determined by the first pressure gauge 200 is in the first pressure band p1, the controller 600 controls the first control valve 400 to be opened to allow the sample gas to flow through the first flow line 300. The first pressure band p1 may be greater than or equal to 500 torr, which is applicable to a thermal chemical vapor deposition process, a diffusion process, or a bake process. If the pressure determined by the first pressure gauge 200 is in the second pressure band p2, the controller 600 controls the second control valve 410 to be opened to allow the sample gas to flow through the second flow line 310. The second pressure band p2 may be greater than or equal to 1 torr and less than 500 torr, which is applicable to most of chemical vapor deposition processes or a diffusion process. If the pressure determined by the first pressure gauge 200 is in the third pressure band p3, the controller 600 controls the third control valve 420 be opened to allow the sample gas to flow through the third flow line 320. The third pressure band p3 may be less than 1 torr.

For example, the controller 600 may be a programmable logic controller.

Figure 7:
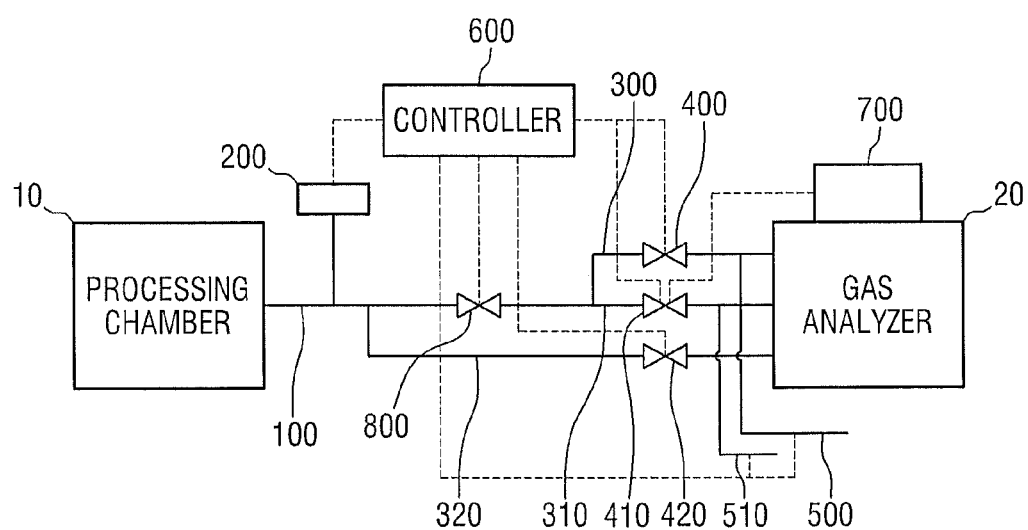
FIG. 7 schematically illustrates an apparatus for providing a sample gas according to another embodiment of the present inventive concept.

FIG. 7 schematically illustrates an apparatus for providing a sample gas according to another embodiment of the present inventive concept. For the sake of convenient explanation, the following description will focus on differences between the apparatuses according to the present and previous embodiments.

Referring to FIG. 7, the sample gas providing apparatus 2 further includes a second pressure gauge 700 and a safety valve 800.

The second pressure gauge 700 measure the pressure of the sample gas exhausted from one of the first to third flow lines 300, 310 and 320. That is to say, if the pressure band is changed (e.g., sharply changed) during the manufacturing process, the second pressure gauge 700 may sense the change (e.g., sharp change) in the pressure band, and the opening or closing rate of the safety valve 800 may be adjusted, which may protect the gas analyzer 20 by adjusting the amount of the sample gas induced into the gas analyzer 20.

The safety valve 800 may adjust the amount of the sample gas flowing through the first or second flow line 300 or 310 according to the pressure measured by the second pressure gauge 700. Since the pressure of the sample gas flowing through the first or second flow line 300 or 310 can be relatively high, it is desirable to cope with the change in the process pressure band.

Figure 8:
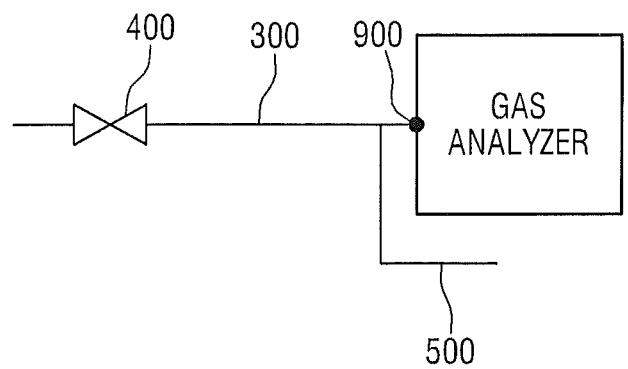
FIG. 8 illustrates a portion of an apparatus for providing a sample gas according to another embodiment of the present inventive concept.
Figure 9:
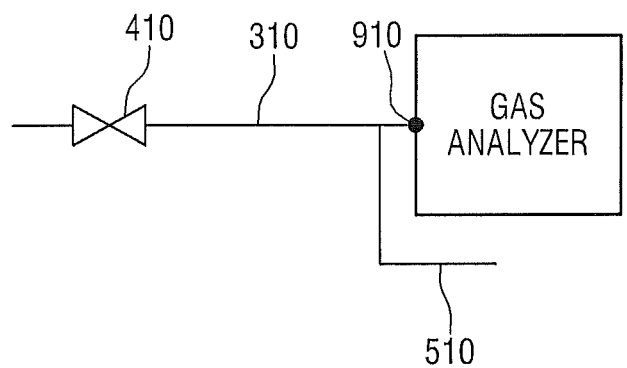
FIG. 9 illustrates a portion of an apparatus for providing a sample gas according to another embodiment of the present inventive concept.

FIG. 8 illustrates a portion of an apparatus for providing a sample gas according to still another embodiment of the present inventive concept, and FIG. 9 illustrates a portion of an apparatus for providing a sample gas according to still another embodiment of the present inventive concept. For the sake of convenient explanation, the following description will focus on differences between the apparatuses according to the present and previous embodiments.

Referring to FIGS. 8 and 9, the first and second flow lines 300 and 310 may include orifices 900 and 910 formed at sample gas exhausting portions, respectively. The orifices 900 and 910 may inhibit or prevent the sample gas from being excessively provided due to a pressure difference between the process chamber 10 and the first and second flow lines 300 and 310, thereby providing an appropriate amount of sample to the gas analyzer 20. For example, diameters of the orifices 900 and 910 may be 20 μm.

Hereinafter, a method for providing a sample gas according to an embodiment of the present inventive concept will be described.

FIG. 10 is a flowchart sequentially illustrating a method for providing a sample gas according to an embodiment of the present inventive concept.

Referring to FIG. 10, a first pressure of induced sample gas is first measured, and one of first to third pressure bands p1, p2 and p3 is determined based on the first pressure (S1000). The first pressure band p1 may be a band greater than or equal to 500 torr, the second pressure band p2 may be a band greater than or equal to 1 torr and less than 500 torr, and the third pressure band p3 may be a band less than 1 torr. For example, when the first pressure is 10 torr, the first pressure gauge 200 determines that the process belongs to the second pressure band p2.

Next, one of first to third control valves 400, 410 and 420 is opened according to the determined one of the first to third pressure bands p1, p2 and p3 (S1100). In the aforementioned example, when the determined pressure band is the second pressure band p2, the second control valve 410 is opened. Thus, the sample gas flows through the second flow line 310.

Next, a second pressure of the sample gas exhausted through one of the first to third flow lines 300, 310 and 320 is measured (S1200). In the aforementioned example, the second pressure of the sample gas exhausted through the second flow line 310 is measured.

Next, an amount of sample gas flowing through the first or second flow line 300 or 310 is adjusted based on the second pressure (S1300). In the aforementioned example, if the second pressure is increased, the safety valve 800 is closed to reduce the amount of sample gas flowing through the second flow line 310. That is to say, the amount of sample gas induced to the gas analyzer 20 is reduced for the purpose of protecting the gas analyzer 20.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims. It is therefore desired that the present embodiments be considered in all respects as illustrative and not restrictive, reference being made to the appended claims rather than the foregoing description to indicate the scope of the inventive concept.

What is claimed is:

1. An apparatus for providing a sample gas to a gas analyzer, the apparatus comprising:
   a gas dosing portion;
   first, second and third flow lines diverging from the gas dosing part portion with each of the first, second and third flow lines extending to and connecting with the gas analyzer;
   a first pressure gauge configured to measure a pressure of a sample gas provided through the gas dosing portion;
   a first control valve configured to be opened and closed, the first control valve disposed in the first flow line;
   a second control valve configured to be opened and closed, the second control valve disposed in the second flow line;
   a third control valve configured to be opened and closed, the third control valve disposed in the third flow line; and
   a controller configured to:
   open the first control valve and close the second and third control valves when the pressure measured by the first pressure gauge is in a first pressure band, thereby allowing the sample gas to flow through the first flow line;
   open the second control valve and close the first and third control valves when the pressure measured by the first pressure gauge is in a second pressure band, thereby allowing the sample gas to flow through the second flow line; and
   open the third control valve and close the first and second control valves when the pressure measured by the first pressure gauge is in a third pressure band, thereby allowing the sample gas to flow through the third flow line.

2. The apparatus of claim 1, further comprising:
   a first bypass line formed in the first flow line for allowing some of the sample gas flowing through the first flow line to be exhausted away from the gas analyzer; and
   a second bypass line formed in the second flow line for allowing some of the sample gas flowing through the second flow line to be exhausted away from the gas analyzer.

3. The apparatus of claim 1, further comprising:
   a second pressure gauge for measuring a pressure of the sample gas exhausted through one of the first and second flow lines, wherein the second pressure gauge is configured and positioned to measure a pressure of the sample gas exhausted through one of the first and second flow lines into the gas analyzer; and
   a safety valve for controlling the amount of the sample gas flowing to the first or second flow line according to the pressure measured by the second pressure gauge.

* * * * *